(12) United States Patent
Schibler et al.

(10) Patent No.: US 8,838,397 B1
(45) Date of Patent: Sep. 16, 2014

(54) REPRESENTING A PLOT WITH A MINI-PLOT

(75) Inventors: James Andrew Schibler, Santa Clara, CA (US); David Gordon Moore, San Francisco, CA (US); Ronald Steven Baron, San Jose, CA (US); Der-Min Fan, Fremont, CA (US); Damon Ray Gragg, Jr., Livermore, CA (US); Hung Vu, San Jose, CA (US)

(73) Assignee: Dionex Corporation, Sunnyvale, CA (US)

( * ) Notice: Subject to any disclaimer, the term of this patent is extended or adjusted under 35 U.S.C. 154(b) by 1001 days.

(21) Appl. No.: 12/626,394

(22) Filed: Nov. 25, 2009

Related U.S. Application Data

(60) Provisional application No. 61/152,643, filed on Feb. 13, 2009.

(51) Int. Cl.
*G01N 31/00* (2006.01)
(52) U.S. Cl.
USPC ............................................................ 702/32

(58) Field of Classification Search
CPC .................................................. G01N 30/8651
USPC ................................................................ 702/32
See application file for complete search history.

(56) References Cited

U.S. PATENT DOCUMENTS

| 6,430,512 B1 * | 8/2002 | Gallagher | 702/22 |
| 6,562,628 B1 | 5/2003 | Liu et al. | 436/161 |
| 7,605,814 B1 * | 10/2009 | Critz | 345/440 |

* cited by examiner

*Primary Examiner* — Stephen Cherry
(74) *Attorney, Agent, or Firm* — Douglas J. Crisman

(57) ABSTRACT

A mini-plot is generated using the actual raw measurement data, and gives a preview of a full-sized plot which is displayed when a user expresses interest in the mini-plot. In some embodiments, the mini-plot is sufficiently resolved to provide the user with graphical information about the measurement data. In some embodiments, the mini-plot is updated upon receiving new measurement data from an ongoing experiment. In some embodiments, the mini-plot is a mini-chromatogram. In some embodiments, the mini-plot is displayed in a table along with textual and/or numerical measurement data for an experiment (e.g., in listing textual and/or numerical chromatography data).

13 Claims, 9 Drawing Sheets

GUI
400

| | Mini-plot | Name | Type | Volume | Instrument Method | Process Method | Injection Time | Status | |
|---|---|---|---|---|---|---|---|---|---|
| 1 | 〰 | ultraSep Water 1 | Unknown | 20.0000 (ul) | MUN-WIS | MUN | 1/23/2008 1:18 PM | Finished | |
| 2 | 〰 | ultraSep Soil | Unknown | 10.0000 (ul) | MUN-WIS | MUN | 1/24/2008 1:18 PM | Finished | |
| 3 | 〰 | E1 EPA 8330 10 ppm | Unknown | 10.0000 (ul) | Acclaim E1 | Acclaim E1 | 1/24/2008 1:18 PM | Finished | |
| 4 | 〰 | E1 EPA 8330 10 ppm | Unknown | 10.0000 (ul) | Acclaim E1 | Acclaim E1 | 1/24/2008 1:18 PM | Idle | |
| 5 | 〰 | E1 EPA 8330 10 ppm | Unknown | 20.0000 (ul) | Acclaim E1 | Acclaim E1 | 1/24/2008 1:18 PM | Finished | |

Columns labeled: 412, 416, 418, 420, 422, 426, 428, 430, 410

Fig. 4

| | Mini-plot | Name | Type | Volume | Instrument Method | Process Method | Injection Time | Status |
|---|---|---|---|---|---|---|---|---|
| 1 | ~~~ | ultraSep Water 1 | Unknown | 20.0000 (ul) | MUN-WIS | MUN | 1/23/2008 1:18 PM | Finished |
| 2 | ~~~ | ultraSep Soil | Unknown | 10.0000 (ul) | MUN-WIS | MUN | 1/24/2008 1:18 PM | Finished |
| 3 | ~~~ | E1 EPA 8330 10 ppm | Unknown | 10.0000 (ul) | Acclaim E1 | Acclaim E1 | 1/24/2008 1:18 PM | Finished |
| 4 | ~~~ | E1 EPA 8330 10 ppm | Unknown | 10.0000 (ul) | Acclaim E1 | Acclaim E1 | 1/24/2008 1:18 PM | Idle |
| 5 | ~~~ | E1 EPA 8330 10 ppm | Unknown | 20.0000 (ul) | Acclaim E1 | Acclaim E1 | 1/24/2008 1:18 PM | Finished |

GUI 400

REPRESENTING A PLOT WITH A MINI-PLOT

RELATED APPLICATIONS

This application claims the benefit of U.S. Provisional Application No. 61/152,643, titled "Representing a Plot with a Mini-Plot" filed Feb. 13, 2009 which application is incorporated by reference herein in its entirety.

This application is related to U.S. patent application Ser. No. 12/359,253, titled "Baseline Alternatives For Unresolved Peaks," filed Jan. 23, 2009, which application is incorporated by reference herein in its entirety.

This application is related to Provisional U.S. Patent Application No. 61/147,083, titled "Workflows for Defining a Sequence for an Analytical Instrument," filed Jan. 24, 2009, which application is incorporated by reference herein in its entirety.

TECHNICAL FIELD

The disclosed embodiments relate generally to generating and displaying outputs of analytical laboratory equipment, and in particular to generating and displaying mini-plots that represent plots of measurement data obtained from analytical laboratory equipment.

BACKGROUND

Chromatography is an analytical technique that generates data in patterns that are quite recognizable to people who are familiar with the technique. Chromatography software typically provides textual displays of sequences, which are defined as sets of chromatographic analyses done in sequential order. Chromatography software typically provides access to the data associated with a particular analysis in a sequence, but this access can be inconvenient in that it is provided in response to a user selecting an analysis in the sequence and opening a separate viewing window to examine the data.

SUMMARY

Some embodiments provide methods, systems, and graphical user interfaces (GUIs) for receiving chromatography data for a plurality of analyses and displaying a plurality of mini-chromatograms associated with at least subset of the plurality of analyses. A respective mini-chromatogram is generated using chromatography data associated with a particular analysis, and is representative of an associated full-sized chromatogram.

In some embodiments the mini-chromatograms are "live," they are updated periodically as new data is received. In some embodiments, the data is received from an ongoing experiment.

In some embodiments, the date is displayed in a tabular format where some of the columns provide textual and/or numerical data associated with a particular analysis and one or more other columns display the mini-chromatograms.

In some embodiments, when a mini-chromatogram is selected, a corresponding full-sized chromatogram is displayed. In some embodiments, the table of mini-chromatograms is displayed in one portion of a display screen and the full-sized chromatogram is simultaneously displayed in a different portion of the display screen.

In some embodiments, when a second mini-chromatogram is selected, a corresponding second full-sized chromatogram is displayed. In some embodiments, the second full-sized chromatogram is displayed overlaying the first full-sized chromatogram. In some embodiments, the two full-sized chromatograms are displayed in a manner that visually distinguishes them from one another and visually associates them with their corresponding mini-chromatograms. In some embodiments, a comparison between the first and second full-sized chromatograms is computed and displayed.

Some embodiments provide methods, systems, and graphical user interfaces for receiving measurement data for a plurality of experiment and displaying a plurality of mini-plots associated with at least a subset of the plurality of experiments. A respective mini-plot is generated using measurement data associated with a particular experiment, and is representative of a full-sized plot. Furthermore, a respective mini-plot is updated upon receiving new measurement data for the corresponding experiment.

In some embodiments, the measurement data generated by an analytical lab instrument is selected from the group consisting of: chromatography instruments, optical spectrometers, nuclear magnetic resonance spectroscopy (NMR) spectrometers, mass spectrometers, radioactivity detectors, refractive index detectors, light scattering detectors, and ultraviolet-visible spectroscopy (UV/Vis) detectors.

Some embodiments provide methods, systems, and graphical user interfaces (GUIs) for receiving chromatography data for at least one analyses and displaying a table having at least two cells. The table includes a first cell listing textual or numerical data associated with the analysis. The table also includes a second cell, displaying a mini-chromatogram associated with the analysis. The mini-chromatogram is generated using chromatography data associated with the analysis. The mini-chromatogram is representative of an associated full-sized chromatogram. In some embodiments, the two cells are in a single row.

BRIEF DESCRIPTION OF THE DRAWINGS

FIG. 4 illustrates an example of a graphical user interface (GUI) showing a table with mini-plots.

Like reference numerals refer to corresponding parts throughout the drawings.

DESCRIPTION OF EMBODIMENTS

Figure 1:
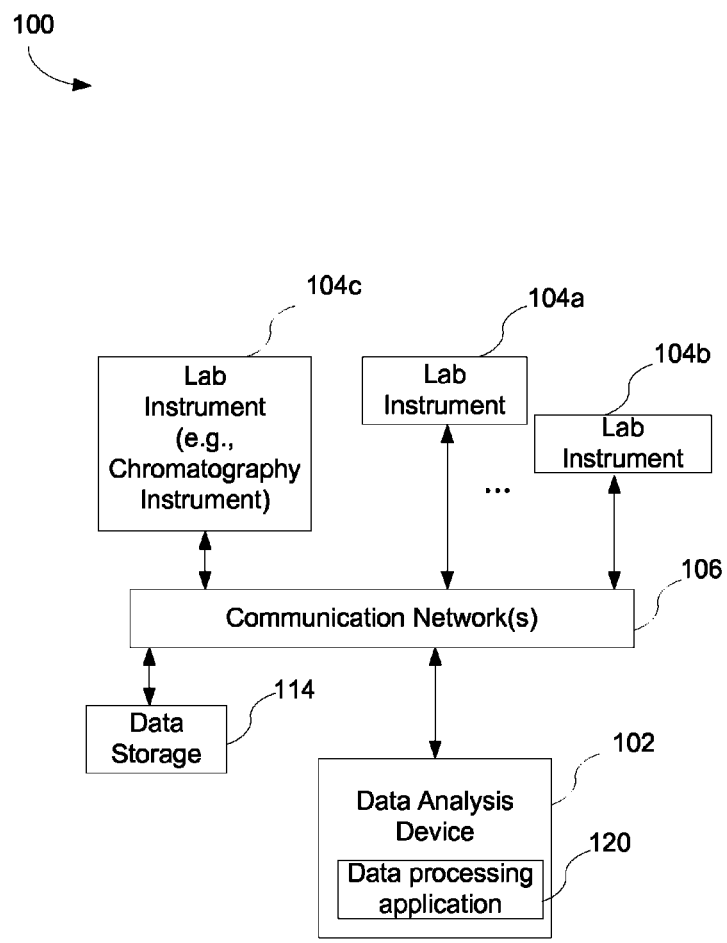
FIG. 1 is a block diagram of a laboratory analysis system according to some embodiments.

According to some embodiments, methods, systems, and user interfaces for presenting laboratory data are described. Specifically, methods, systems, and user interfaces for providing a convenient preview of laboratory data are described.

For ease of discussion, in the embodiments described here, a chromatography system is described in which an application program is used to present chromatography data. In other embodiments, application programs employing at least some similar techniques render visual representations of data generated by other types of analytical lab instruments, such as optical spectrometers, nuclear magnetic resonance spectroscopy (NMR) spectrometers, mass spectrometers, radioactivity detectors, refractive index detectors, light scattering detectors, and ultraviolet-visible spectroscopy (UV/Vis) detectors. Other detectors that can be used are described in U.S. Pat. No. 6,562,628 Entitled, "Electrolytic Suppressor and Separate Eluent Generator Combination," incorporated herein by reference.

In some embodiments, described below, an application (e.g., a chromatography application) automatically generates a table to display textual and/or numeric information corresponding to output data of analytical laboratory equipment and mini-plots representative of full-sized plots corresponding to the output data. For the purpose of this invention table means any structured presentation of data comprising at least one row and at least one column. A mini-plot has a size that is substantially smaller than the full-sized plot. The mini-plot is produced based on actual output data and is placed into the table. The full-sized plot is generated and/or retrieved and displayed if the user indicates interest in the mini-plot. Further, in some embodiments, a mini-plot is updated as more output data is received, for instance, from an ongoing experiment.

The table with the mini-plots can provide a convenient preview of the full-sized plot data. In some embodiments, a user can instantly get a clear sense of the raw output data by looking at the corresponding mini-plot. User can also scan and visually compare raw data in order to confirm consistency and spot anomalies. User can locate an analysis of interest visually, instead of having to rely on textual and/or numeric information or on opening the full output or measurement data array. In these ways, large amounts of useful information can be instantaneously communicated to a user in a natural and intuitive visual manner.

In the chromatography context, mini-plots can be generated for chromatograms (which typically map to injections), spectra (which can map to individual compounds, many of which can be in a specific chromatogram), contour plots to render 3-D data, plots to render processed signals (for example, a subtracted signal trace or the second derivative of a signal), and plots to render other types of data that may have different types of correspondence than per-injection or per-compound. By looking at the mini-plot, the user can visually recognize and compare the peak patterns of different analyses, and spot anomalies (such as injection with too few or too many peaks, misshaped peaks, baselines shifts, and so on).

FIG. 1 is a block diagram of a laboratory analysis system 100. The laboratory analysis system 100 includes one or more laboratory instruments 104 (such as a chromatography instrument 104c) in communication with a data analysis device 102 and a data storage device 114. The data analysis device 102 has stored thereon a data processing application 120 for analyzing experimental data received from the one or more laboratory instruments 104 and/or experimental data imported from other data analysis devices or other laboratory analysis systems. In some embodiments, the data processing application 120 is a chromatography application 120. Laboratory instruments 104, the data storage device 114 and the data analysis device 104 may communicate with each other using one or more communications network(s) 106 or may be connected to each other without using any communication network 106, such as by use of a USB, RS-232, IEEE, or LAN cable/connection. The communications network(s) 106 can be any of a number of network types (e.g. Internet, intranet, local area network, wide area network, wireless network, wired network, optical network, etc.).

The data analysis device 102 analyzes data produced as a result of processes being performed at the laboratory instruments 104, and which may be stored in the data storage device 114. The data analysis device 102 can also analyze data imported from another system.

In particular, the data processing application 120 executing on the data analysis device 102 analyzes the data output. For instance, the data processing application 120 may be a chromatography application 120 that produces a chromatogram as the visual output of chromatography instrument 104c.

FIG. 1 is a functional depiction of the various features. In practice, and as recognized by those of ordinary skill in the art, items shown separately could be combined and some items could be separated.

Figure 2:
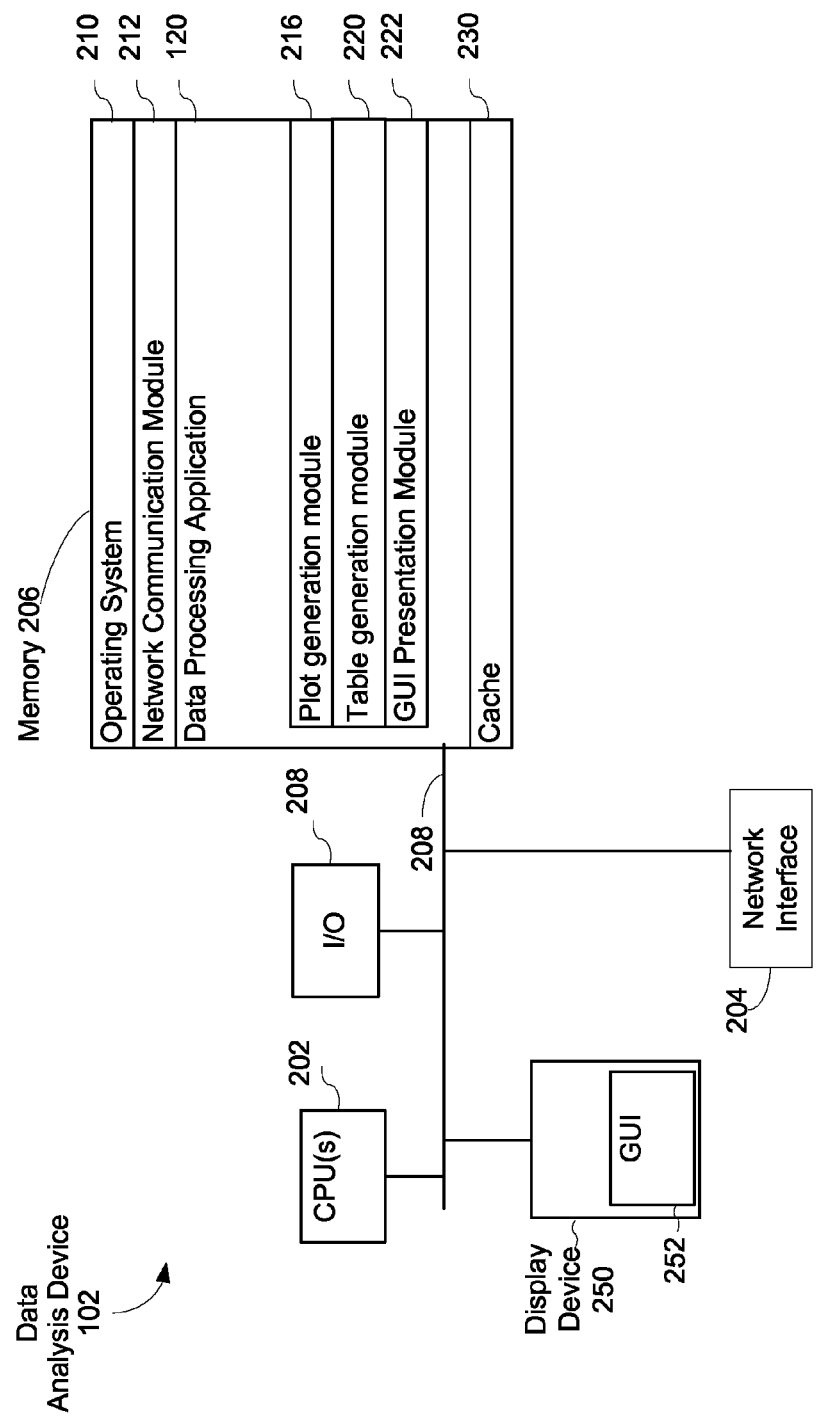
FIG. 2 is a block diagram illustrating a data analysis device with a data processing application according to some embodiments.

FIG. 2 illustrates a block diagram of a data analysis device 102. The data analysis device 102 generally includes one or more processing units (CPU's) 202, one or more network or other communications interfaces 204, memory 206, an input device 208 (such as keyboard, mouse, and the like), an output device 250, such as a display device 250, and one or more communication buses 208 for interconnecting these components. The display device 250 may be used to render a user interface 252 (such as, a graphical user interface (GUI)) associated with the operation of chromatography application 120. Communication buses 208 may include circuitry (sometimes called a chipset) that interconnects and controls communications between system components. Memory 206 includes high-speed random access memory, such as DRAM, SRAM, DDR RAM or other random access solid state memory devices; and may include non-volatile memory, such as one or more magnetic disk storage devices, optical disk storage devices, flash memory devices, or other non-volatile solid state storage devices. Memory 206 may optionally include one or more storage devices remotely located from the CPU(s) 202. Memory 206, or alternately the non-volatile memory device(s) within memory 206, comprises a computer readable storage medium. In some embodiments, memory 206 stores the following programs, modules and data structures, or a subset thereof:

- an operating system 210 that includes procedures for handling various basic system services and for performing hardware dependent tasks;
- an optional network communication module 212 that may be used for connecting data an analysis device 102 to other computers via one or more communication network interfaces 204 (wired or wireless) and one or more communication networks, such as the Internet, other wide area networks, local area networks, metropolitan area networks, and so on;
- a data processing application 120 for analyzing an output data array produced as a result of processes being performed at the laboratory instruments 104. The processing application 120 includes a plot generation module 216 to generate mini-plots and full-sized plots based upon the data array and user preferences (such as, scaling preferences). A mini-plot has a size that is substantially smaller than a full-sized plot. For instance, a mini-plot may be less than one-fourth the size of a full-sized plot. In some embodiments, the plot generation module 216 updates a mini-plot as more output data is received, for instance, from an ongoing experiment. The data processing application 120 includes a table generation module 220 to generate a table to display (i) textual and/or numeric information corresponding to output data of analytical laboratory equipment (e.g., laboratory instruments 104) and (ii) mini-plots representative of full-sized plots corresponding to the output data. The data processing application 120 includes a GUI presentation module 222 to present a graphical user interface (GUI) to display the table generated by the table generation module 220, and to display a corresponding full-sized plot in response to a user selection of a mini-plot; and a data cache 230 to store data used and/or produced by the various programs 120 including, for instance, textual and/or numeric information corresponding to output data of analytical laboratory equipment (e.g., laboratory instruments 104), full sized plots generated by the plot generation module 216, user preferences, default settings, and so on.

Each of the above identified elements may be stored in one or more of the previously mentioned memory devices, and corresponds to a set of instructions for performing a function described above. The above identified modules or programs (i.e., sets of instructions) need not be implemented as separate software programs, procedures or modules, and thus various subsets of these modules may be combined or otherwise re-arranged in various embodiments. In some embodiments, memory 206 may store a subset of the modules and data structures identified above. Furthermore, memory 206 may store additional modules and data structures not described above.

Figure 3:
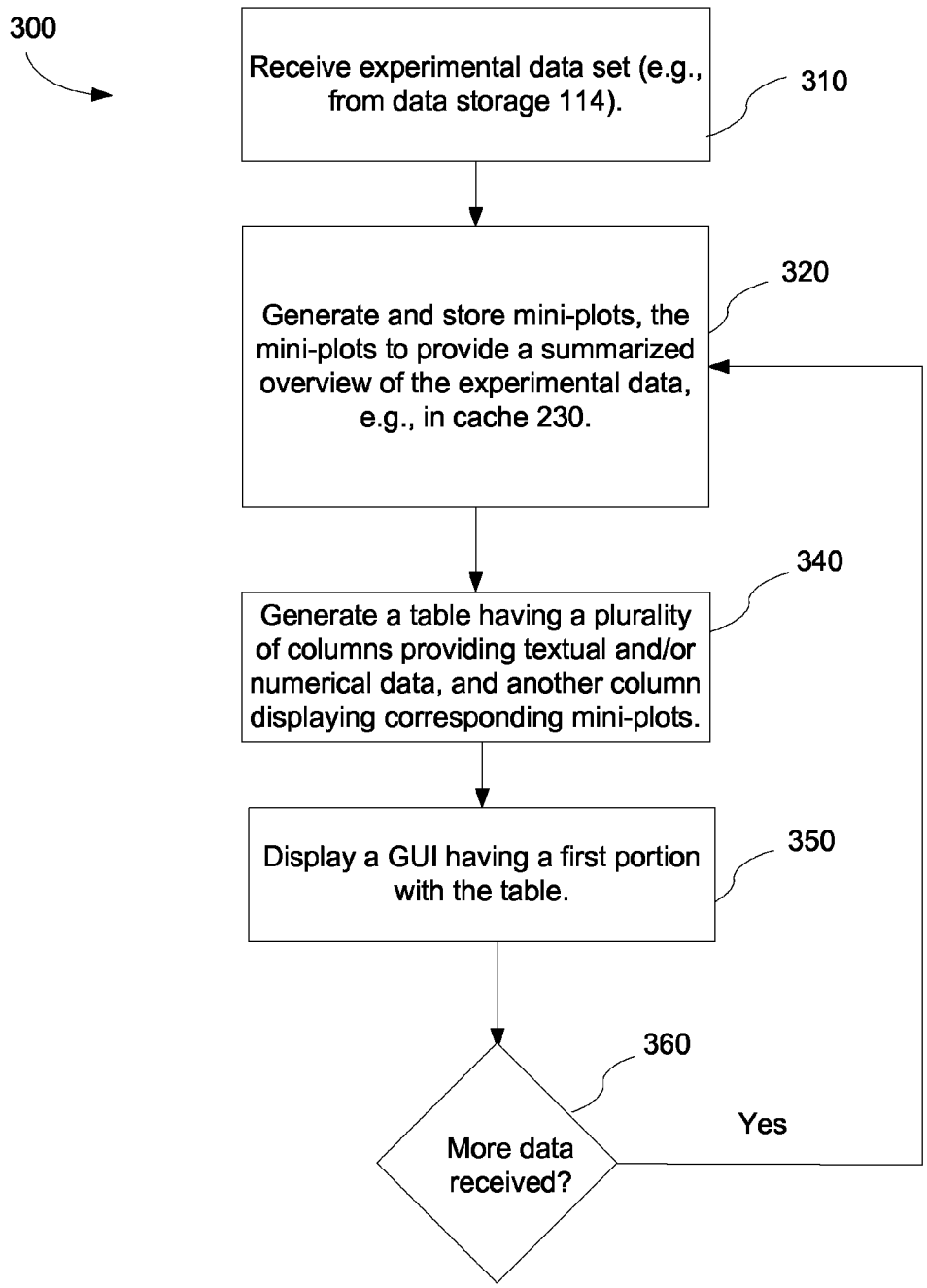
FIG. 3 is a flow diagram of a process performed by the data processing application to display mini-plots according to some embodiments.

FIG. 3 is a flowchart representing a method 300 performed by the data processing application 120 to display mini-plots according to certain embodiments. The data processing application 120 receives an experimental data array (310). The data array is a discrete set of raw or processed data that is normally considered as a logical unit. For instance, in the context of chromatography, examples of a chromatography data array include: a chromatogram; a spectrum; a multi-dimensional detector signal; a profile of eluent composition, pressure, temperature, pH, on/off state, or another system parameter over the time period of an individual analysis; and a trend plot representing measurement of a parameter or result over a time period encompassing multiple individual analyses. In some embodiments, the data processing application 120 receives, as the data array, data produced as a result of processes being performed at the laboratory instruments 104, which may be stored in the data storage device 114 and/or data imported from another system.

The plot generation module 216 generates mini-plots based on the data array (320) and stores the generated mini-plots, for instance, in cache 230. In some embodiments, the plot generation module 216 generates mini-plots using the same user preferences that are used to control generation of the full-sized plots by the full-sized plot generation module 216. For instance, scaling of the data array for generating the mini-plots may be controlled by the same user preferences that are used to control scaling of full-sized displays of the same data. For example, if the user specifies scaling of the full-sized plot to the tallest peak, then the mini-plot is also scaled using the tallest peak. In this way, a user can optimize mini-plot displays to show portions of the data array of greatest interest. Further, generating mini-plots using the same user preferences that are used to control generation of the full-sized plots can ensure that the user gets an expected result when going from the mini-plot to the corresponding full-sized plot. In some embodiments, the plot generation module 216 processes the mini-plot by using one or more of: auto-scaling, reducing resolution, and down-sampling, so that the generated mini-plots will fit within the dimensions of a table cell, and have enough resolution so as to convey meaningful information to a user.

The table generation module 220 generates a table having a plurality of columns that list textual and/or numerical information related to the received data array, and another column that displays corresponding mini-plots (340). In some embodiments, the table generation module 220 generates the table without requiring explicit user input regarding which textual and/or numerical information to display. The table generation module 220 may use a combination of rules that are based on one or more of: filter criteria entered by a user, queries entered by the user, and/or default parameters. The GUI presentation module 222 displays a GUI that includes the table and one or more other portions (350).

In some embodiments, a user can optionally alter the size of the mini-plots by adjusting the column width and/or row height of the column that displays the mini-chromatograms. In some embodiments, in response to receiving the adjustments to the column dimensions, the plot generation module 216 redraws the mini-plots to fit the new dimensions.

Further, in some embodiments, the mini-plots are "live" in the sense that they are updated as the data array from which they are generated is updated. In these embodiments, if the data processing application 120 receives more data, e.g., for an ongoing sequence (360), the plot generation module 216 re-generates the mini-plot based on the updated data array, and the GUI presentation module 222 updates the GUI (e.g., GUI 300) with the updated mini-plot. Optionally, the GUI presentation module 222 also visually emphasizes (e.g., by changing a background color) the row for which the mini-plot is updated, thus notifying the user of the change.

As an example, in the chromatography context, the data processing application 120 receives data for injections of one or more sequences (e.g., from data storage 114). The plot generation module 216 generates mini-chromatograms for each injection of a sequence. The table generation module 220 generates a table having a plurality of columns list textual and/or numerical information related to the received data array, and another column that displays corresponding mini-chromatograms. The GUI presentation module 222 displays a GUI that includes the table (350) and one or more other portions. An example of such a GUI is illustrated in FIG. 4.

FIG. 4 illustrates an example of a GUI 400 that displays a table 410 having columns 416-430 that display textual and/or numerical information related to variables associated with the received data array and a column 412 that displays associated mini-chromatograms. Although only one mini-chromatogram is shown for each row of table 410, in other embodiments, more than one mini-chromatogram may be displayed. For instance, mini-chromatograms representing multiple detector channels (e.g. conductivity+UV, or several selected UV wavelengths), or a detector signal and a pressure trace may be displayed.

As illustrated in the table 410, a column 416 displays the name of the sample, a column 418 lists an injection type, a column 420 lists the volume, a column 422 lists the instrument method, a column 426 lists the processing method, a column 428 lists an injection time, and a column 430 lists an injection status (e.g., finished or idle). Alternatively or in addition, textual and/or numerical information related to other variables, including custom variables defined by a user, can be listed in the table 410. In some embodiments, the order of presentation of the columns in Table 410 can be specified by the user. The table 410 thus enables a user to browse through data arrays by displaying textual and/or numerical information in columns 416-430 and also a small graphical sample represented by the mini-chromatograms 412.

The mini-chromatograms 412 enable a user to get a sense of the raw data associated with each analysis. Further, the user can scan and visually compare the raw data in order to confirm consistency and spot anomalies. Also, the user can locate an analysis of interest visually, instead of having to rely on textual information or open the full data array. Thus, the mini-chromatograms 412 communicate useful information to a chromatographer in a fast, natural, and intuitive visual manner.

Figure 5:
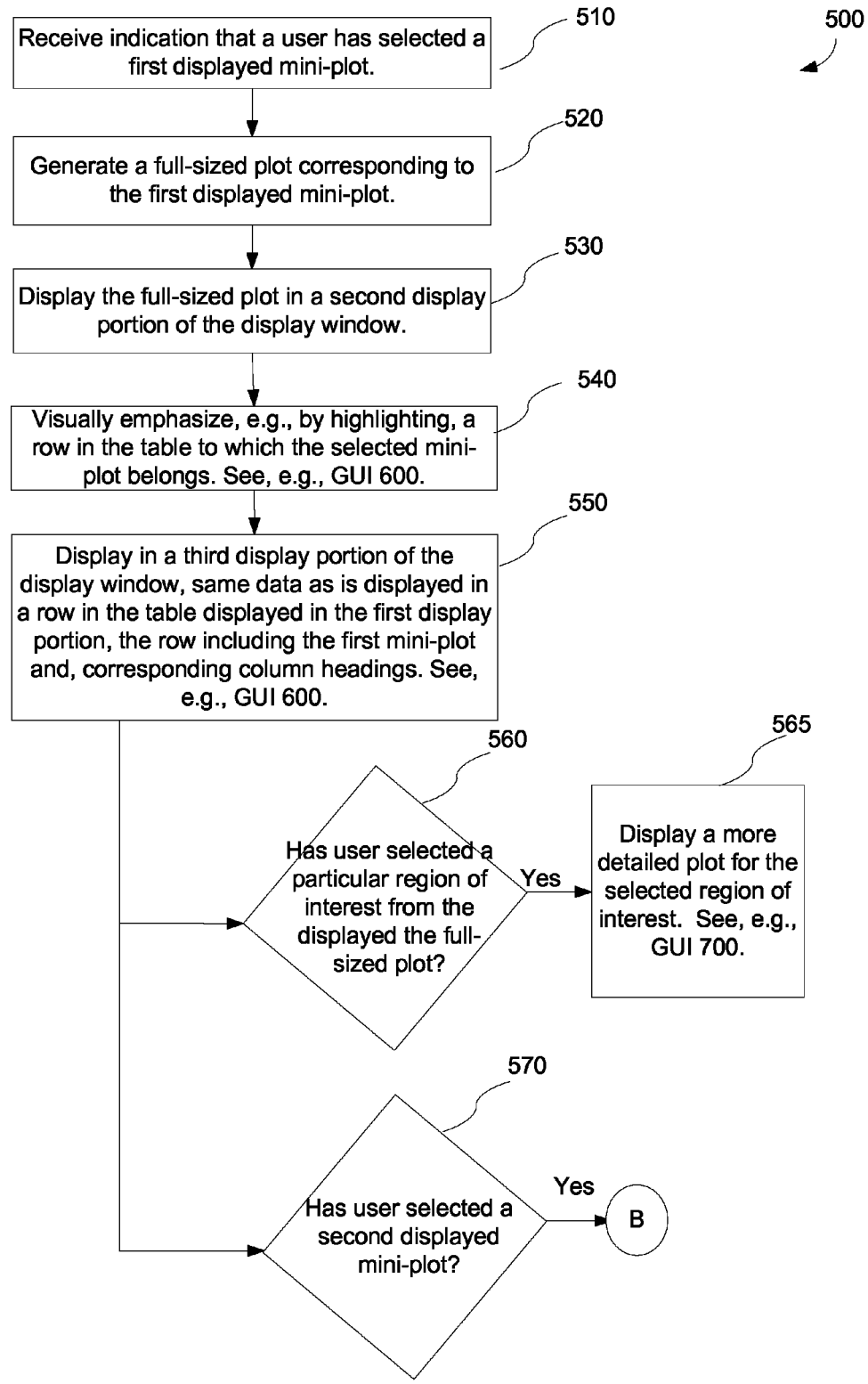
FIG. 5 is a flow diagram of a process performed by the data processing application to display full-sized plots according to some embodiments.

FIG. 5 is a flowchart representing a method 500 performed by the data processing application 120 to display full-sized plots. The data processing application 120 receives an indication that a user has selected or otherwise expressed interest in a first displayed mini-plot (510). A user may express interest in a first displayed mini-plot for instance, by hovering a mouse on a first displayed mini-plot, by a single (e.g., right click) or double click of the mouse, and so on. This first displayed mini-plot may be a plot at any location in the table, not necessarily in the first row, as may be specified by a user in some embodiments.

The plot generation module 216 generates a full-sized plot for the same data array used to generate the first displayed mini-plot (520). In some embodiments, the full-sized plot is generated on the fly (e.g., in response to receiving an indication that the user has selected the first displayed mini-plot.) In other embodiments, the full-sized plot is generated at an earlier time (e.g., at a time the mini-plot is generated), and stored, e.g., in the cache 230.

The GUI presentation module 220 displays the full-sized plot in a second portion of the GUI (530). In some embodiments, the GUI presentation module 220 also visually emphasizes, e.g., by highlighting, at least a portion of the row (in the table) to which the selected mini-plot belongs (540). The visual emphasis indicates to the user that the displayed full-sized plot corresponds to the data in the visually emphasized row.

In some embodiments, the GUI presentation module 220 also displays the textual and/or numerical information in the row in the table to which the selected mini-plot belongs in a third portion of the GUI (530). Doing so can provide a convenient way for providing the textual and/or numerical information associated with the displayed full-sized plot in a display area that is adjacent to the displayed full-sized plot.

Figure 6:
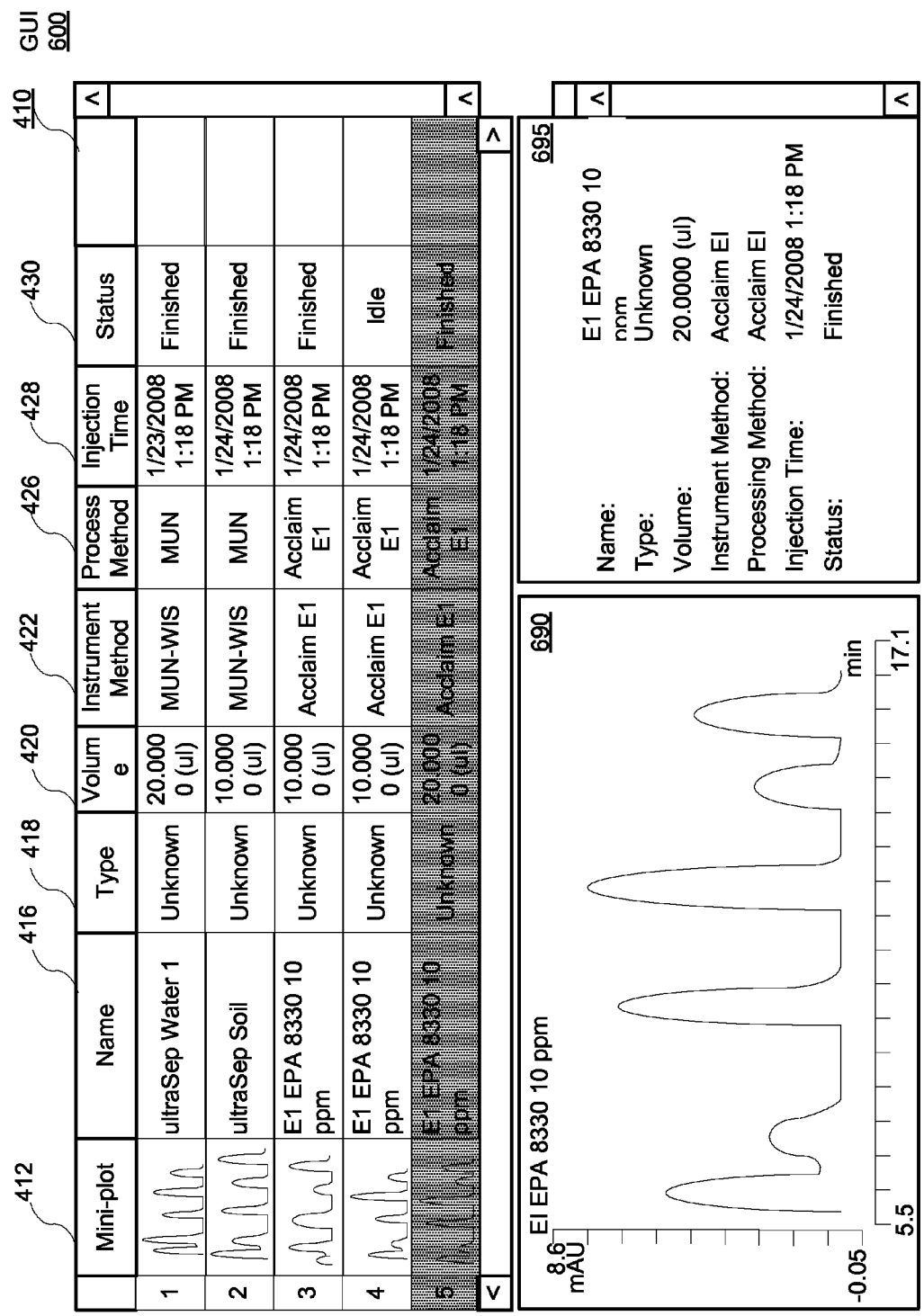
FIGS. 6 and 7 illustrate examples of a graphical user interface (GUI) showing full-sized plots.

FIG. 6 illustrates a GUI 600 that is similar to GUI 400, except that a user has expressed interest in the mini-chromatogram in the fifth row of the table 410. The fifth row is visually emphasized, and a full-sized chromatogram corresponding to the mini-chromatogram in the fifth row is depicted in GUI portion 690. Additionally, a listing of the textual and/or numerical information associated with the displayed full-sized chromatogram is depicted in a GUI portion 695.

Referring back to FIG. 5, a user can also zoom into the displayed full-sized plot. If the user selects a particular region of interest from the displayed full-sized plot (560), the GUI presentation module 220 presents a more detailed plot of the selected region of interest (565).

Figure 7:
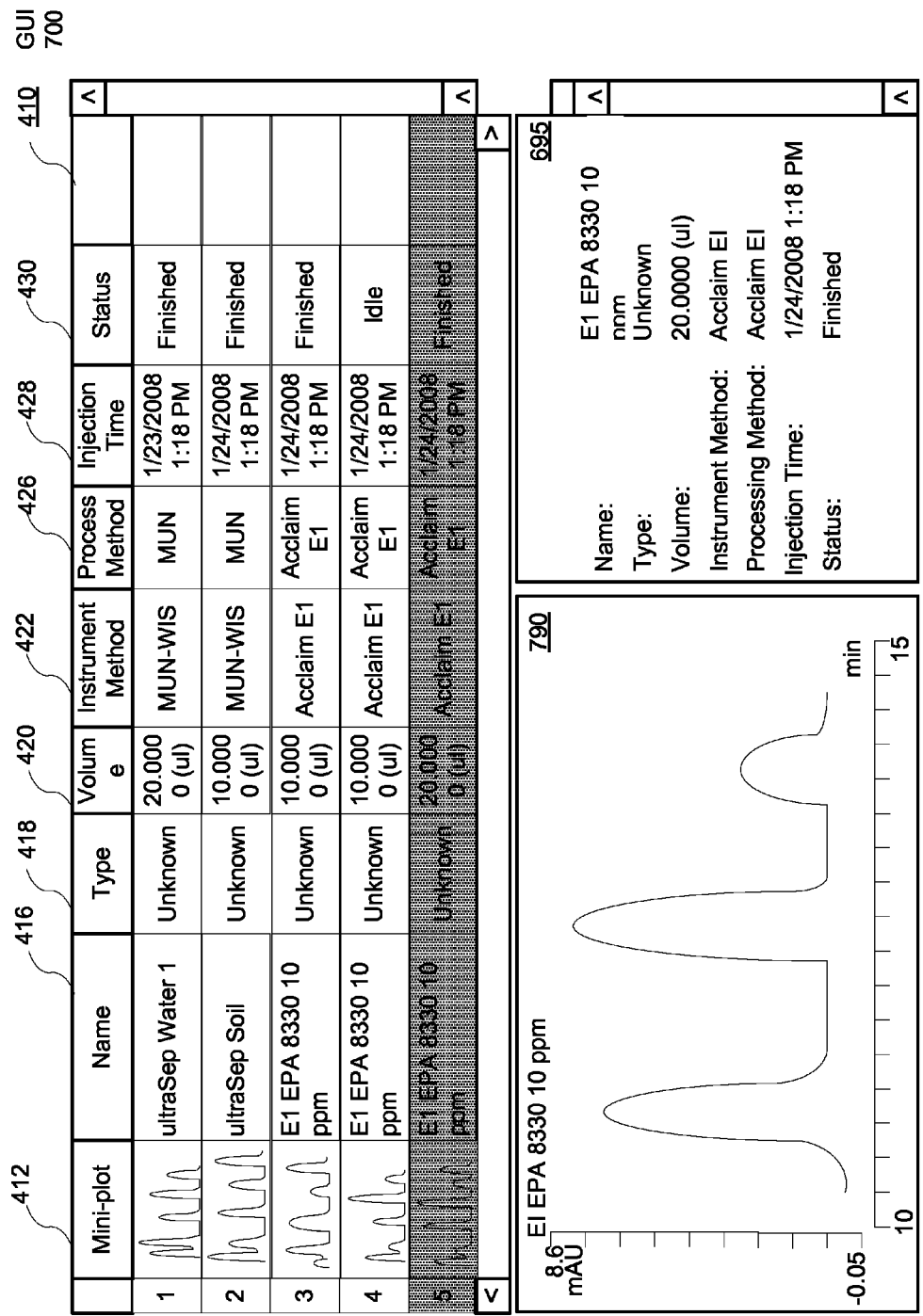

FIG. 7 illustrates a GUI 700 that is similar to the GUI 600, except that in response to user interest in a particular region of the full-sized chromatogram depicted in GUI portion 690, a more detailed plot of the full-sized chromatogram for the selected region of interest is displayed in GUI portion 790. Comparing FIGS. 6 and 7, in FIG. 6, the chromatogram displayed in GUI portion 690 covers a range of 5.5 to 17.1 minutes, while in FIG. 7, the chromatogram displayed in the GUI portion 790 covers a range of 10 to 15 minutes.

Figure 8:
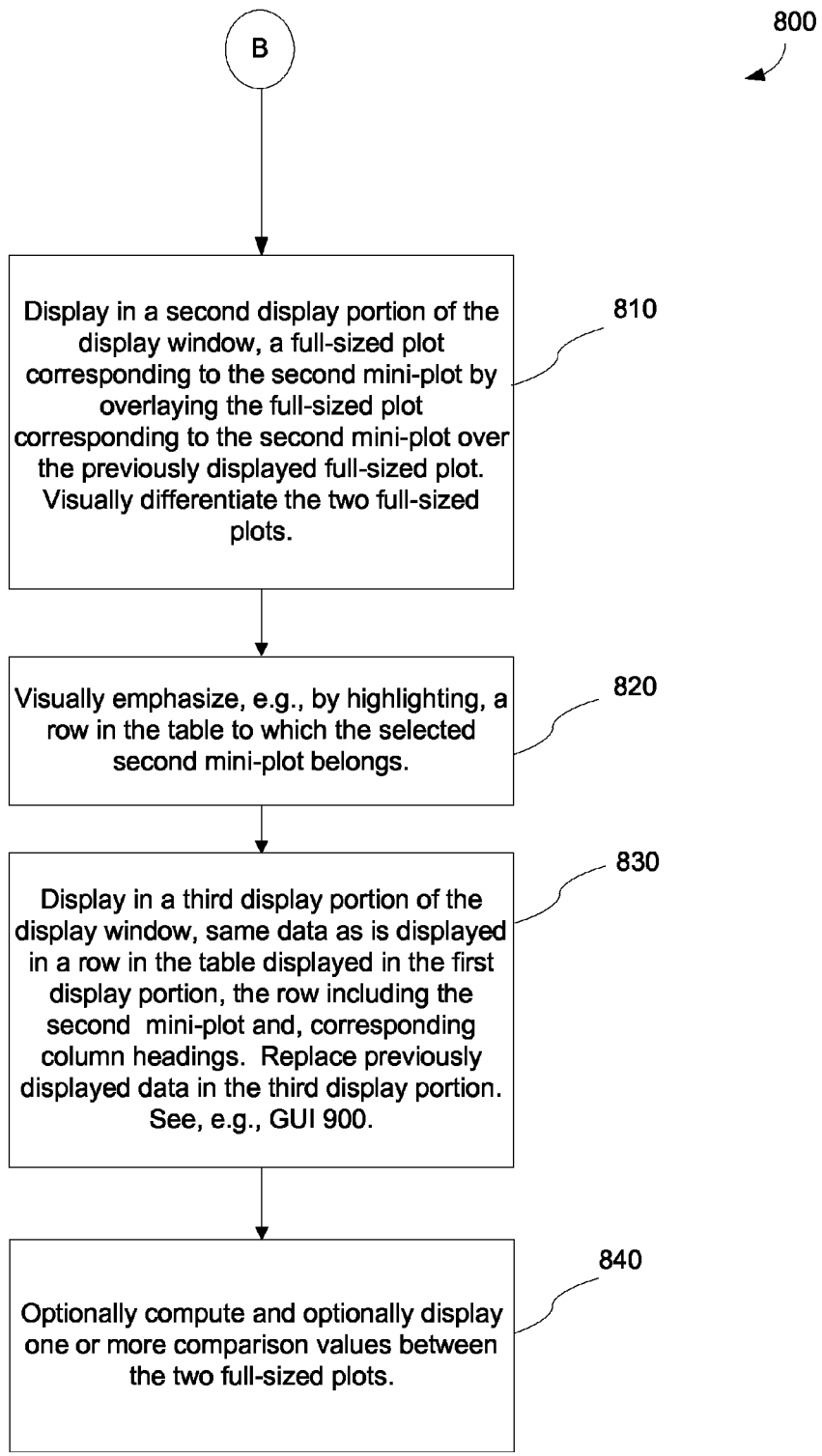
FIG. 8 is a flow diagram of a process performed by the data processing application to display full-sized plots according to some embodiments.

Referring back to FIG. 5, a user can express interest in other displayed mini-plots (570), in response to which the corresponding full-sized plot is displayed together with the previously displayed full-sized plot, as discussed further in reference to FIG. 8. The plots displayed together may be viewed in a "stacked" format, with each plot having its own set of axes, or in an "overlaid" format in which all the plots share the same set of axes, or in a "mixed" format, in which plots of the same data type share axes, and a separate set of axes appears in a stacked format for each different data type. FIG. 8 illustrates a process 800 performed by a data processing application 120 (FIG. 2) when a user expresses interest in more than one displayed mini-plot.

The GUI presentation module 220 displays in the second display portion of the display window (e.g., GUI portion 590), a full-sized plot corresponding to the second selected mini-plot by overlaying the full-sized plot corresponding to the second selected mini-plot over the previously displayed full-sized plot (810). In some embodiments, the GUI presentation module 220 visually differentiates the two full-sized plots.

In some embodiments, the GUI presentation module 220 also visually emphasizes, e.g., by highlighting, at least a portion of the row (in the table) to which the selected second mini-plot belongs (820). The GUI presentation module 220 also displays the textual and/or numerical information in the row in the table to which the selected second mini-plot belongs in a third portion of the GUI, e.g., in a portion 690 (830). In some embodiments, only the textual and/or numerical information for the most recently selected mini-plot is depicted in the third portion of the GUI, e.g., in the portion 690, thus replacing the displayed textual and/or numerical information for the preceding mini-plot.

In some embodiments, the data processing application 120 optionally computes and displays one or more values that enable a user to compare the full-sized plots (840). For instance, in the case of spectra, the data processing application 120 optionally computes and displays a level of match between the full-sized plots corresponding to the first and second mini-plots.

Figure 9:
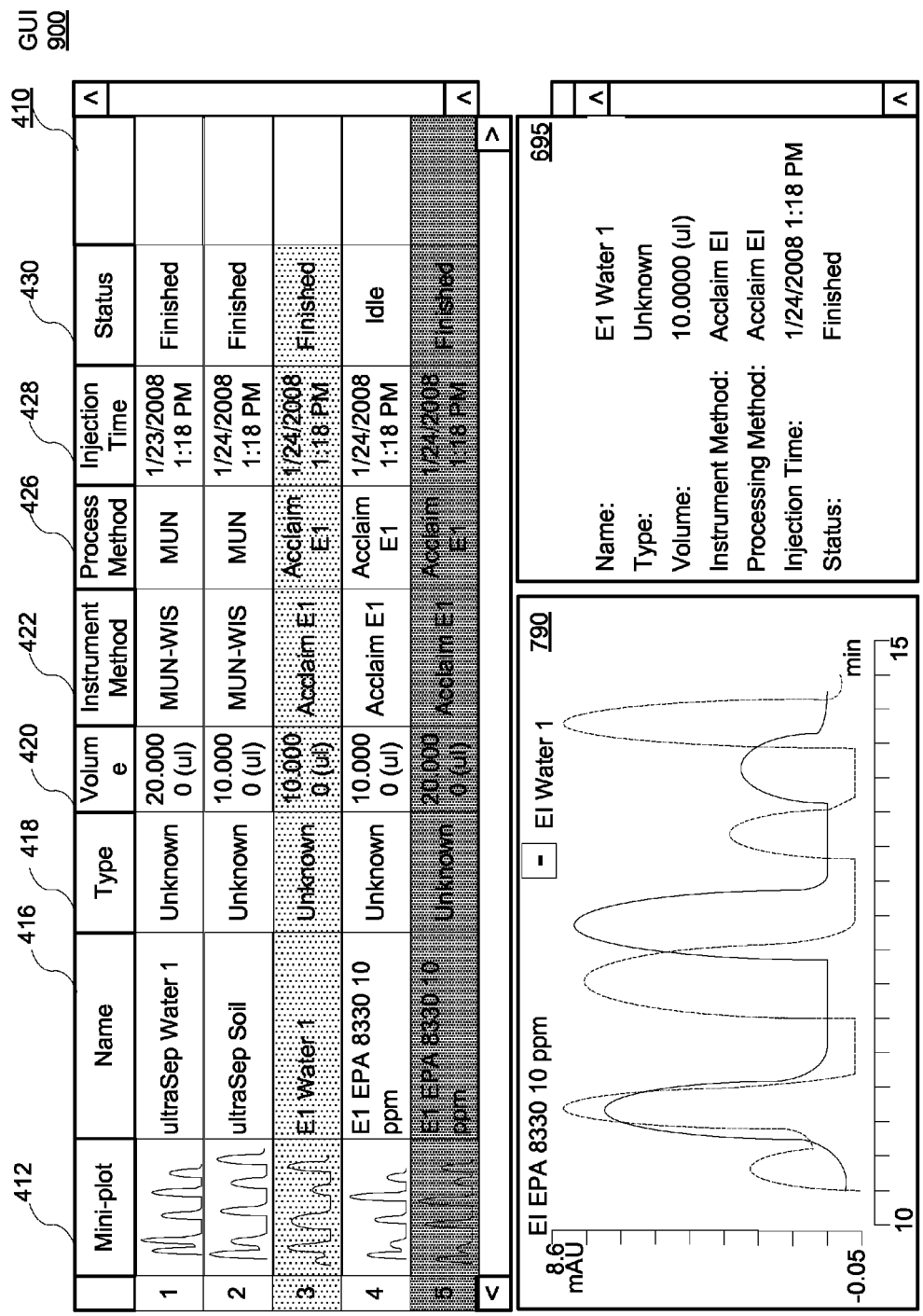
FIG. 9 illustrates an example of a graphical user interface (GUI) showing two overlaid full-sized plots.

FIG. 9 illustrates a GUI 900 that is similar to the GUI 600, except that a user has expressed interest in a second mini-plot in the third row of the table 410. The third row of the table 410 is visually emphasized, and a full-sized chromatogram corresponding to the mini-chromatogram in the third row is overlaid on the full-sized chromatogram corresponding to the mini-chromatogram in the fifth row depicted in GUI portion 990. As illustrated in FIG. 9, the full-sized chromatograms are visually differentiated from each other. Furthermore, as illustrated in FIG. 9, the full-sized chromatograms are visually associated with their corresponding mini-chromatograms (e.g. the third row, is shaded lightly and the corresponding full-sized chromatogram is also shaded lightly.) Additionally, a listing of the textual and/or numerical information associated with the most recently selected mini-chromatogram is depicted in GUI portion 995.

The methods 300, 500 and 800 may be governed by instructions that are stored in a computer readable storage medium and that are executed by one or more processors (e.g., the CPU(s) 202) of the data analysis device 102. Each of the operations shown in FIGS. 3, 5 and 8 may correspond to instructions stored in a computer memory or computer readable storage medium. The computer readable storage medium may include a magnetic or optical disk storage device, solid state storage devices such as Flash memory, or other non-volatile memory device or devices. The computer readable instructions stored on the computer readable storage medium are in source code, assembly language code, object code, or another instruction format that is interpreted by one or more processors.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated.

What is claimed is:

1. A method of processing chromatography data, comprising:
on a computer system having one or more processors and memory storing one or more programs for execution by the one or more processors:
receiving chromatography data for a plurality of analyses;
displaying a plurality of mini-chromatograms associated with at least a subset of the plurality of analyses, wherein a respective mini-chromatogram generated using chromatography data associated with a particular analysis, and wherein the mini-chromatogram is representative of an associated full-sized chromatogram;
wherein the displaying further comprises:
in a first display portion of a display window, displaying a table having:
one or more first columns, each first column listing one of textual and numerical data associated with a particular analysis in the plurality of analyses, and
one or more second columns, each second column displaying, for each row of the table, a respective mini-chromatogram associated with the particular analysis;
updating at least one mini-chromatogram upon receiving new measurement data from an ongoing experiment for an associated one of the analyses so that the mini-chromatogram displays live intermediate results associated with the new measurement data for the ongoing experiment;
in response to user selection of a first mini-chromatogram, displaying a first full-sized chromatogram generated using the chromatography data used to generate the first mini-chromatogram; and
in response to user selection of a second mini-chromatogram, overlaying and simultaneously displaying the first full-sized chromatogram with a second full-sized chromatogram associated with the second mini-chromatogram on a common set of axes.

2. The method of claim 1, further comprising:
updating a plurality of the displayed mini-chromatograms upon receiving new measurement data from a plurality of instruments performing the plurality of analyses.

3. The method of claim 2, wherein respective new measurement data includes data from an ongoing experiment.

4. The method of claim 1, further comprising, for a respective row, displaying a plurality of mini-chromatograms each corresponding to a respective detector channel of multiple detector channels supplying chromatography data.

5. The method of claim 1, further comprising:
displaying the first mini-chromatogram in a visually differentiated manner from the second mini chromatogram and the first full-size chromatogram in a visually differentiated manner from the second full-sized chromatogram; and
displaying the first mini-chromatogram in a visually associated manner with the first full-sized chromatogram and the second mini-chromatogram in a visually associated manner with the second full-sized chromatogram.

6. The method of claim 5, wherein displaying the first mini-chromatogram in a visually associated manner with the first full-sized chromatogram, includes displaying the first mini-chromatogram and the first full-sized chromatogram with similar shading.

7. The method of claim 1, further comprising:
computing and displaying one or more values representing a comparison between the first and second full-sized chromatograms.

8. The method of claim 1, further comprising:
processing the chromatography data for one of the analyses to generate an associated mini-chromatogram, wherein the processing includes at least one of: auto-scaling, reducing resolution, and down-sampling.

9. The method of claim 1, further comprising:
processing the chromatography data for one of the analyses to generate an associated mini-chromatogram, wherein the processing includes scaling the chromatography data for a first analysis using user preferences for generating a full-sized chromatogram.

10. The method of claim 1, further comprising:
in response to user adjustment of one or more of column width and row height of the table, adjusting the mini-chromatograms to fit in corresponding new cell dimensions.

11. The method of claim 1, wherein textual and numerical data associated with a particular analysis includes one or more of: a name, an injection type, a volume, an instrument method, a processing method, an injection time, an injection status, and a user defined custom variable.

12. A system, comprising:
one or more processors;
memory; and
one or more programs stored in the memory, the one or more programs comprising instructions for:
receiving chromatography data for a plurality of analyses; and
displaying a plurality of mini-chromatograms associated with at least a subset of the plurality of analyses, wherein a respective mini-chromatogram is generated using chromatography data associated with a particular analysis, and wherein the mini-chromatogram is representative of an associated full-sized chromatogram;
wherein the instructions for displaying further comprise instructions for displaying:
in a first display portion of a display window, displaying a table having:
one or more first columns, each first column listing one of textual and numerical data associated with a particular analysis in the plurality of analyses, and
one or more second columns, each second column displaying, for each row of the table, a respective mini-chromatogram associated with the particular analysis;

updating at least one mini-chromatogram upon receiving new measurement data from an ongoing experiment for an associated one of the analyses so that the mini-chromatogram displays live intermediate results associated with the new measurement data for the ongoing experiment;

in response to user selection of a first mini-chromatogram, displaying a first full-sized chromatogram generated using the chromatography data used to generate the first mini-chromatogram; and in response to user selection of a second mini-chromatogram, overlaying and simultaneously displaying the first full-sized chromatogram with a second full-sized chromatogram associated with the second mini-chromatogram on a common set of axes.

13. A non-transitory computer readable storage medium storing one or more programs configured for execution by a computer, the one or more programs comprising instructions for:

receiving chromatography data for a plurality of analyses; and displaying a plurality of mini-chromatograms associated with at least subset of the plurality of analyses, wherein a respective mini-chromatogram is generated using chromatography data associated with a particular analysis, and wherein the mini-chromatogram is representative of an associated full-sized chromatogram;

wherein the instructions for displaying further comprise instructions for displaying:

in a first display portion of a display window, displaying a table having:

one or more first columns, each first column listing one of textual and numerical data associated with a particular analysis in the plurality of analyses, and one or more second columns, each second column displaying, for each row of the table, a respective mini-chromatogram associated with the particular analysis;

updating at least one mini-chromatogram upon receiving new measurement data from an ongoing experiment for an associated one of the analyses so that the mini-chromatogram displays live intermediate results associated with the new measurement data for the ongoing experiment;

in response to user selection of a first mini-chromatogram, displaying a first full-sized chromatogram generated using the chromatography data used to generate the first mini-chromatogram; and in response to user selection of a second mini-chromatogram, overlaying and simultaneously displaying the first full-sized chromatogram with a second full-sized chromatogram associated with the second mini-chromatogram on a common set of axes.

* * * * *